(12) United States Patent
Lyons et al.

(10) Patent No.: US 11,433,171 B2
(45) Date of Patent: Sep. 6, 2022

(54) BLOOD CHAMBER LID HAVING INTEGRATED BLOOD FILTER AND VENT

(71) Applicant: ILLINOIS TOOL WORKS INC., Glenview, IL (US)

(72) Inventors: Gregory Thomas Lyons, Woodstock, IL (US); Michael Grant Leonhard, West Bend, WI (US); Robert Warren Cameron, III, Highland, IN (US); Yash Siddhartha, Chicago, IL (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 35 days.

(21) Appl. No.: 16/899,204

(22) Filed: Jun. 11, 2020

(65) Prior Publication Data

US 2020/0390957 A1 Dec. 17, 2020

Related U.S. Application Data

(60) Provisional application No. 62/860,389, filed on Jun. 12, 2019.

(51) Int. Cl.
*A61M 1/30* (2006.01)
*A61M 1/36* (2006.01)

(52) U.S. Cl.
CPC ............ *A61M 1/306* (2014.02); *A61M 1/304* (2014.02); *A61M 1/3633* (2013.01); *A61M 2205/02* (2013.01); *A61M 2205/7545* (2013.01)

(58) Field of Classification Search
CPC .... A61M 1/306; A61M 1/304; A61M 1/3633; A61M 2205/7545; A61M 2205/02; A61M 1/3627
See application file for complete search history.

(56) References Cited

U.S. PATENT DOCUMENTS

| | | | |
|---|---|---|---|
| 7,871,391 B2 | 1/2011 | Folden et al. | |
| 7,938,967 B2 | 5/2011 | Folden et al. | |
| 8,142,383 B2 | 3/2012 | Dannenmaier et al. | |
| 10,213,541 B2 | 2/2019 | Silvestri et al. | |
| 10,251,992 B2 | 4/2019 | Spickermann et al. | |
| 2003/0144646 A1* | 7/2003 | Se | A61M 1/02 604/409 |
| 2011/0118648 A1* | 5/2011 | Katsuno | A61M 1/3627 604/6.15 |

* cited by examiner

*Primary Examiner* — Krishnan S Menon
(74) *Attorney, Agent, or Firm* — Pauley Erickson & Swanson (57) ABSTRACT

A lid for closing an open ended blood chamber is provided. The lid is a one piece device forming an inlet to the blood chamber. The one piece device includes a filter media spaced apart from the inlet and wherein blood passing through the inlet passes through the filter media upon entry into the blood chamber. The filter media filters gross particulate from the blood passing therethrough. The one piece device further includes a vent port with an associated vent port cover to allow air separated to vent from the blood chamber.

19 Claims, 6 Drawing Sheets

BLOOD CHAMBER LID HAVING INTEGRATED BLOOD FILTER AND VENT

CROSS REFERENCE TO RELATED APPLICATION

This application claims the benefit of U.S. Provisional Application, Ser. No. 62/860,389, filed on 12 Jun. 2019. This U.S. Provisional Application is hereby incorporated by reference herein in its entirety and are made a part hereof, including but not limited to those portions which specifically appear hereinafter.

BACKGROUND OF THE INVENTION

Field of the Invention

This invention relates generally to blood treatment and processing and, more particularly, to a blood chamber lid having an integrated blood filter and vent.

Description of Prior Art

The treatment and processing of blood, including the extracorporeal treatment and processing of blood, is well-known. In such treatment and processing, it is common to employ a chamber for a blood treatment system, the chamber having a blood inlet and a blood outlet, a filter element for filtration of the blood and a vent to permit the discharge or release of air or other gaseous material.

Currently it is common for filters and vent caps for blood chambers to be produced by separate machines and subsequently assembled, joined or fastened, such as by or with solvent bonding, with or to a lid for the blood chamber.

Unfortunately, conventional blood treatment processing systems and associated devices, such as blood chambers, are more complicated than desired to manufacture, produce and/or operate such as due to the number of component parts and the consequent complexity in the proper and appropriate assembly and resulting operation.

In view of the above, there is an ongoing need and demand for improved devices for use in the treatment and processing of blood.

SUMMARY OF THE INVENTION

A general object of the invention is to provide improvements in blood treatment and processing. A more specific object of the invention is to provide an improved blood chamber lid. One aspect of the invention focuses on the development of a blood chamber lid having an integrated blood filter and vent.

In one embodiment, a lid for closing an open ended blood chamber is provided. The lid is desirably a one piece device that forms an inlet to the blood chamber. The one piece device includes a filter media spaced apart from the inlet and wherein blood passing through the inlet passes through the filter media upon entry into the blood chamber. The filter media can desirably serve such as to filter gross particulate from the blood passing therethrough. The one piece device further desirably includes a vent port such as with an associated vent port cover to allow air to vent from the blood chamber.

A lid for closing an open ended blood chamber in accordance with another embodiment is desirably a one piece device forming an inlet to the blood chamber. The one piece device has or includes an outline planar shape that conforms to an outline planar shape of the blood chamber open end. The one piece device preferably includes a filter media spaced apart from the inlet and wherein blood passing through the inlet passes through the filter media upon entry into the blood chamber with the filter media filtering gross particulate from the blood passing therethrough. The filter media desirably includes a multi-planar element having a slope angled away from the inlet and toward a lateral side wall of the chamber. The one piece device further includes a vent port, such as with an associated vent port cover, to allow air to vent from the blood chamber.

A lid for closing an open ended blood chamber in accordance with another embodiment is a one piece device forming an inlet to the blood chamber. The one piece device at least in part is formed of an acrylic material and includes a filter media at least one of heat sealed or ultrasonic welded with the acrylic material forming the lid. The filter media is spaced apart from the inlet such that blood passing through the inlet passes through the filter media upon entry into the blood chamber with the filter media filtering gross particulate from the blood passing therethrough. The one piece device further includes a vent port, such as with an associated vent port cover, to allow air to vent from the blood chamber. The vent port cover is desirably composed of an in mesh material.

As used herein, references to the treatment or processing of blood for the filtering or removal of "gross particulate" is to be understood to generally refer to the filtering or removal of any gross particulate, clots, clumps of platelets, etc. or the like from the blood being processed through or with the filter media, element or device.

Other objects and advantages will be apparent to those skilled in the art from the following detailed description taken in conjunction with the appended claims and drawings.

DESCRIPTION OF PREFERRED EMBODIMENTS

The subject development provides improvements in blood treatment and processing. More particularly and as detailed further below, the subject development provides an improved blood chamber lid with particular emphasis on a blood chamber lid having an integrated blood filter and vent.

Figure 1:
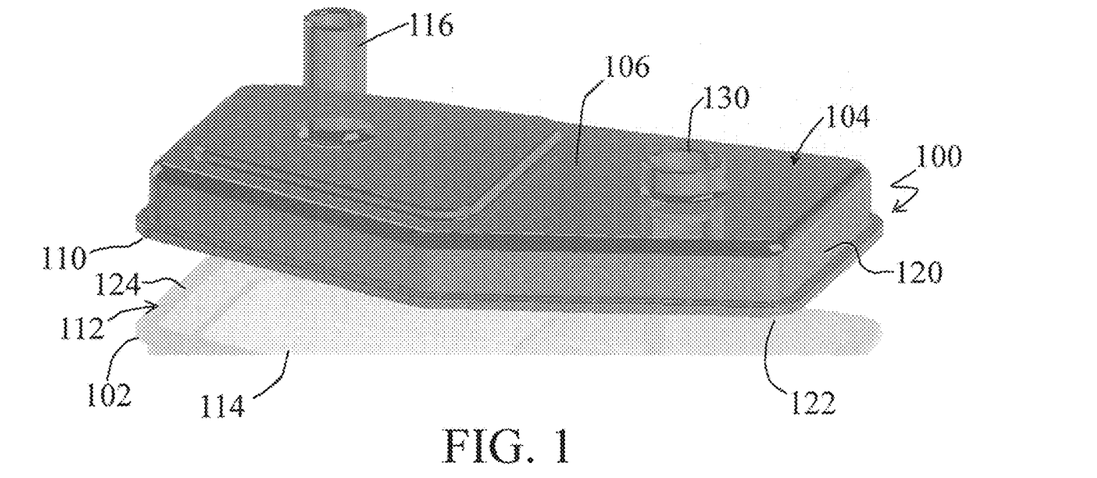
FIG. 1 is a partially exploded fragmentary perspective view of a blood chamber with a blood chamber lid in accordance with one embodiment of the invention.

FIG. 1 illustrates a blood chamber assembly, generally designated by the reference numeral 100, including a blood chamber 102 and a blood chamber lid 104 in accordance with one aspect of the subject invention development. The blood chamber lid 104 is further shown and illustrated in FIGS. 2 and 3.

Figure 2:
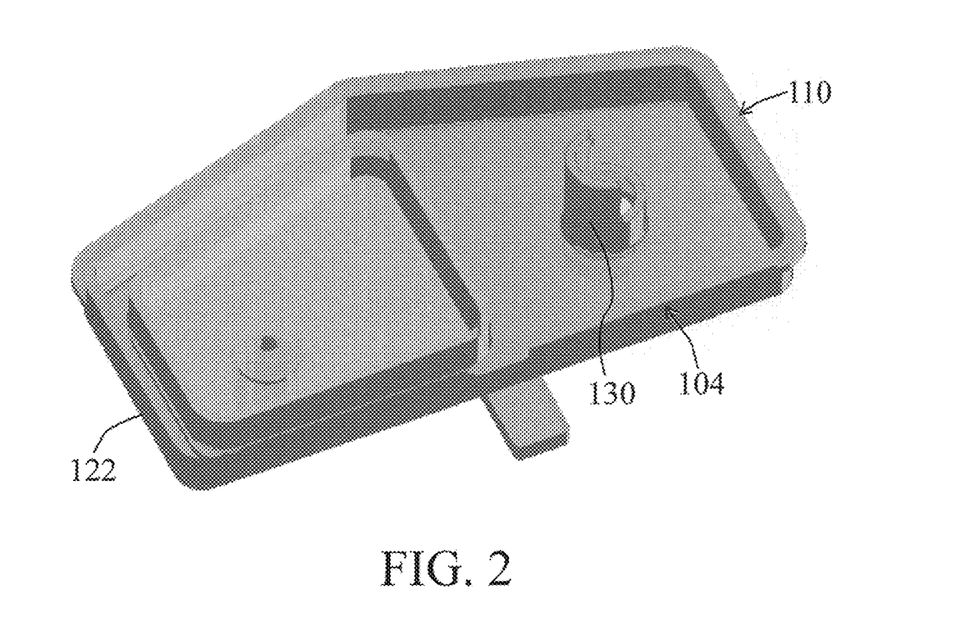
FIG. 2 is a bottom perspective view of the blood chamber lid shown in FIG. 1
Figure 3:
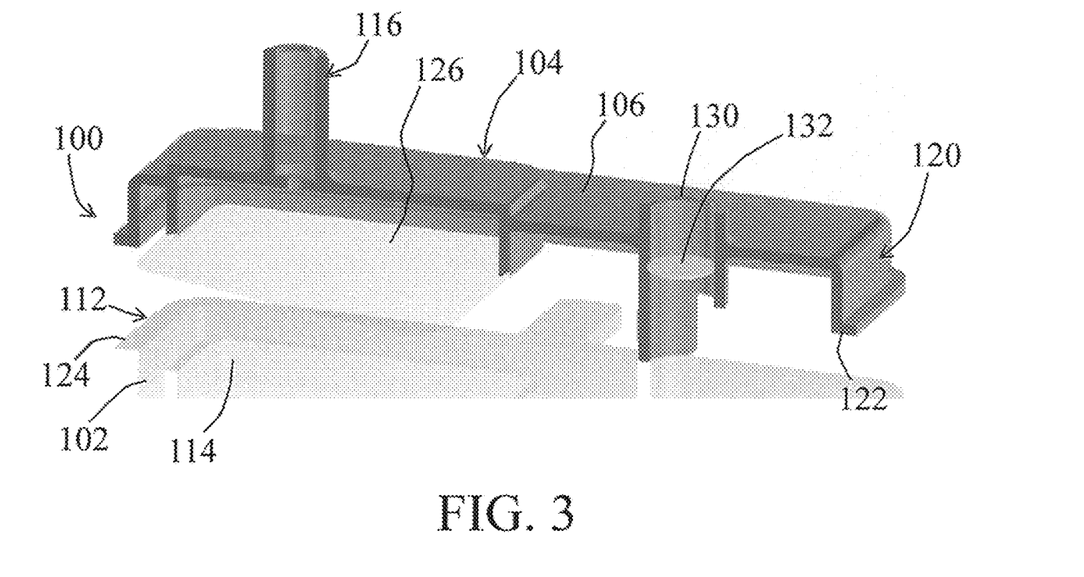
FIG. 3 is a perspective sectional view of the blood chamber lid shown in FIG. 1.
Figure 4:
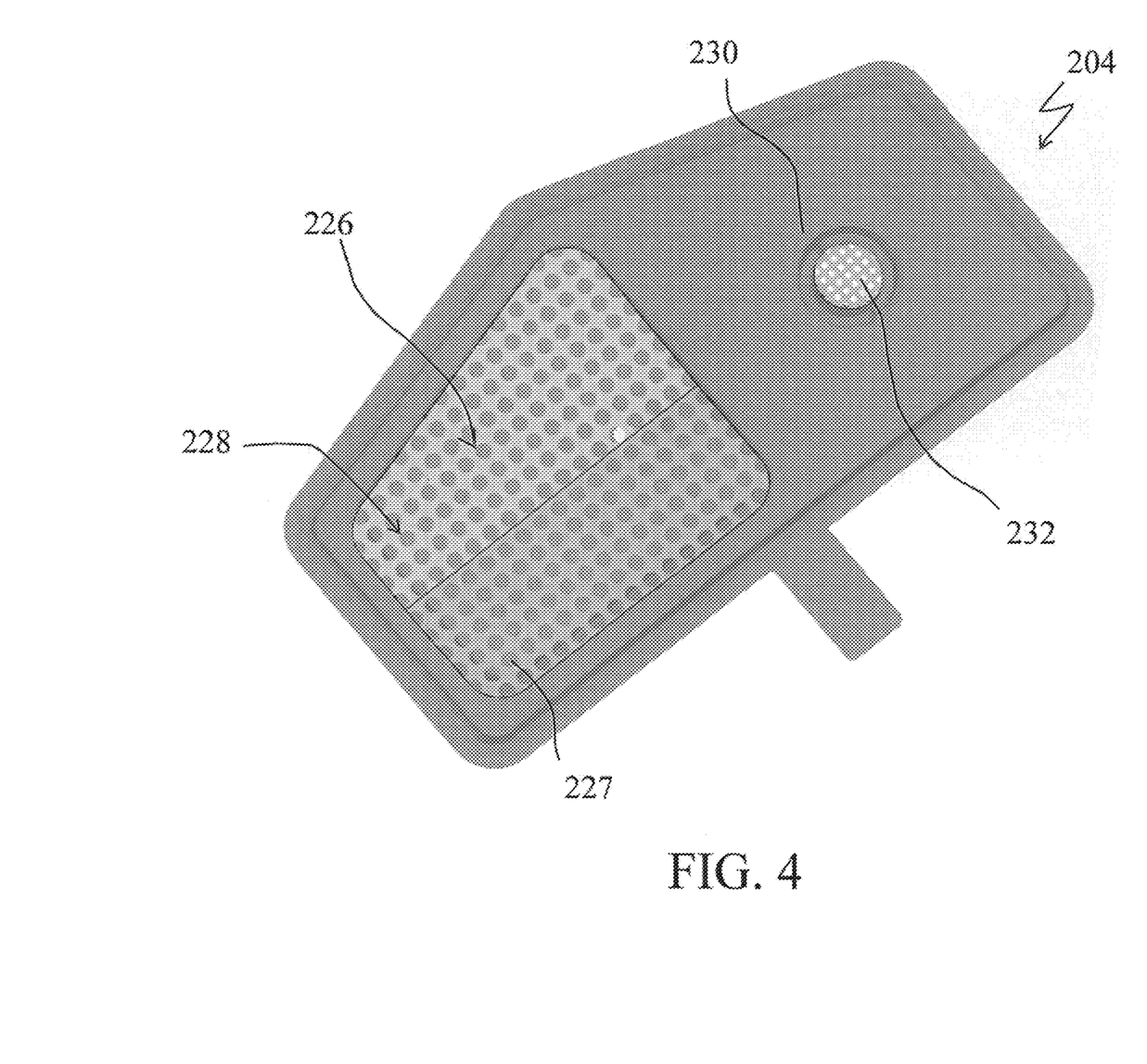
FIG. 4 is a bottom view of a blood chamber lid in accordance with another embodiment of the invention.
Figure 5:
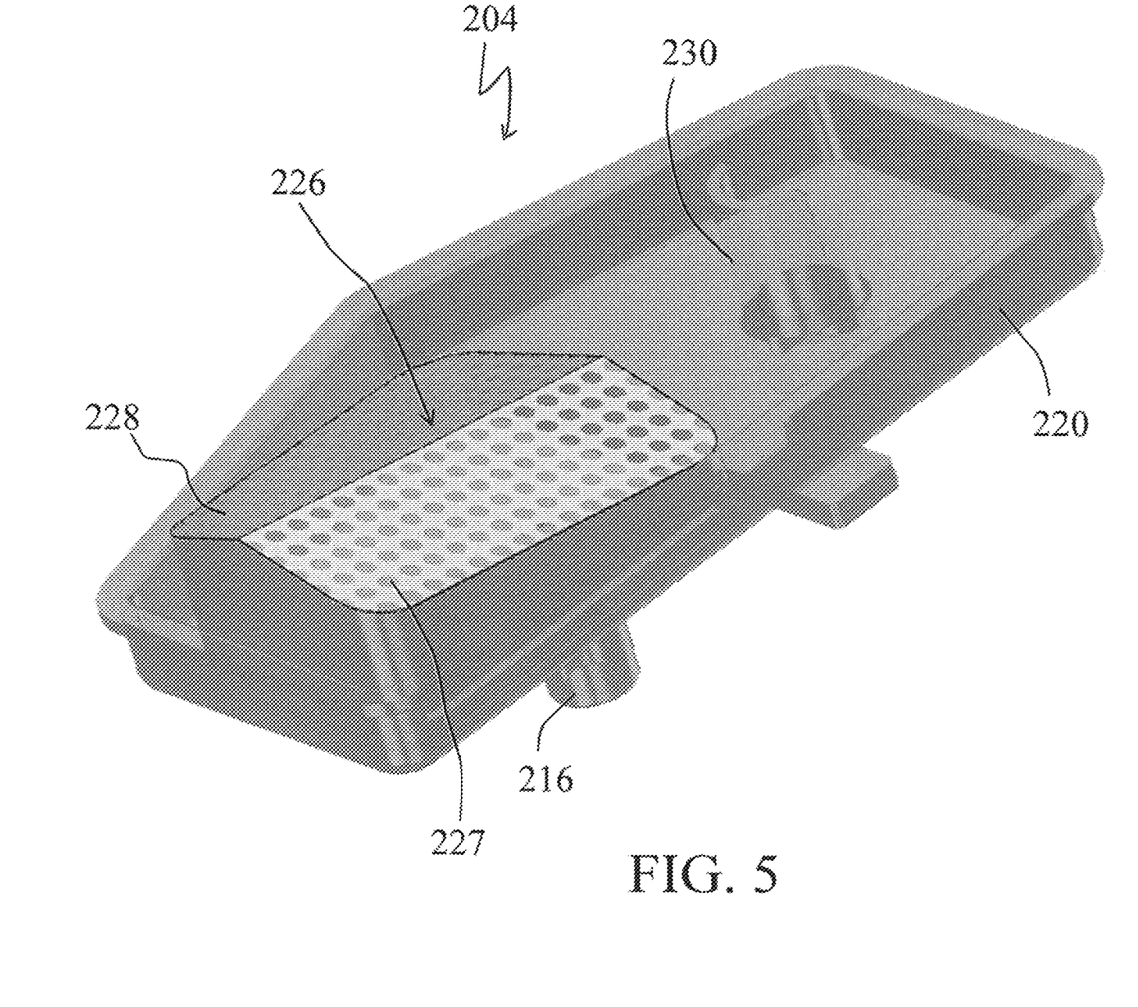
FIG. 5 is a perspective bottom angled view of the blood chamber lid shown in FIG. 4.
Figure 6:
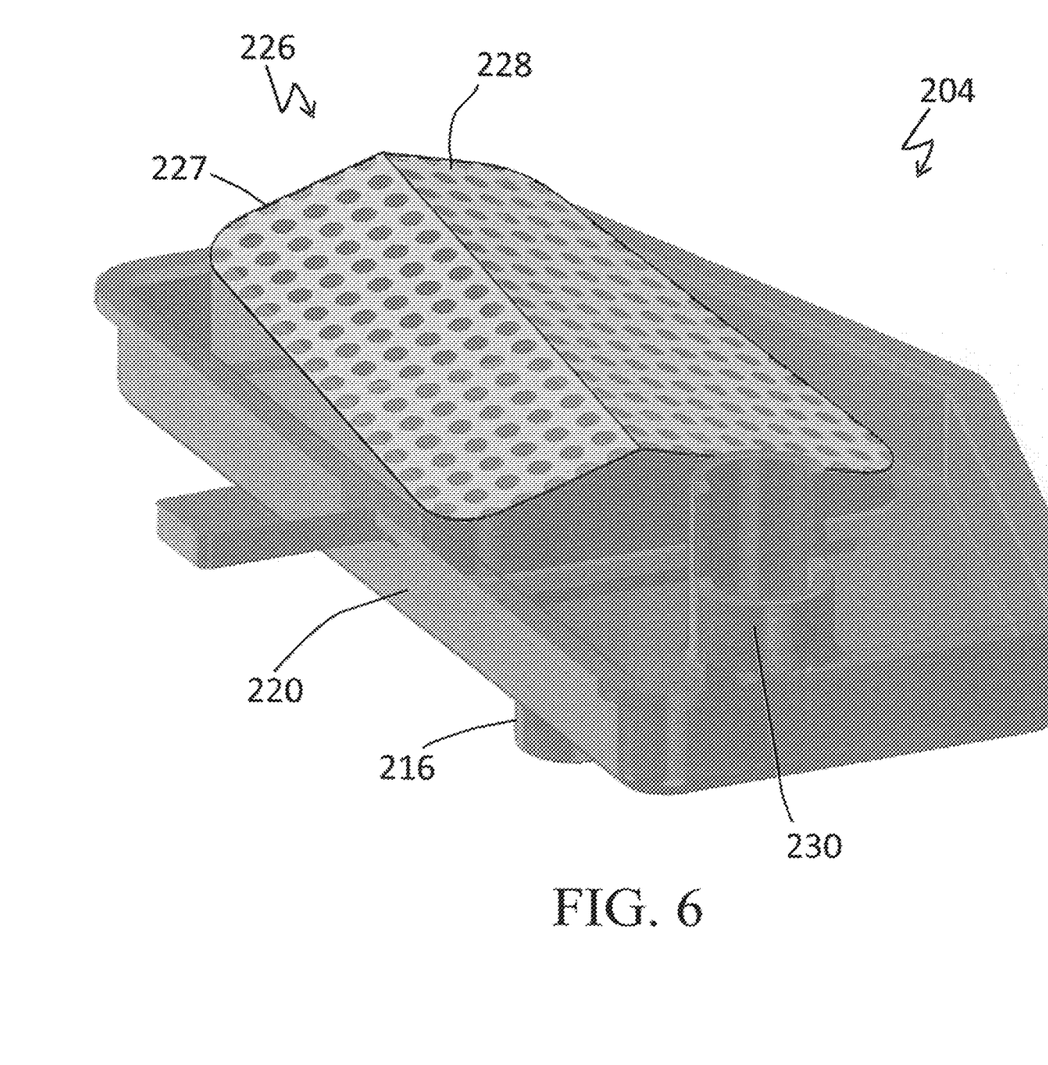
FIG. 6 is another perspective bottom angled view of the blood chamber lid shown in FIG. 4, taken from a different angle.
Figure 7:
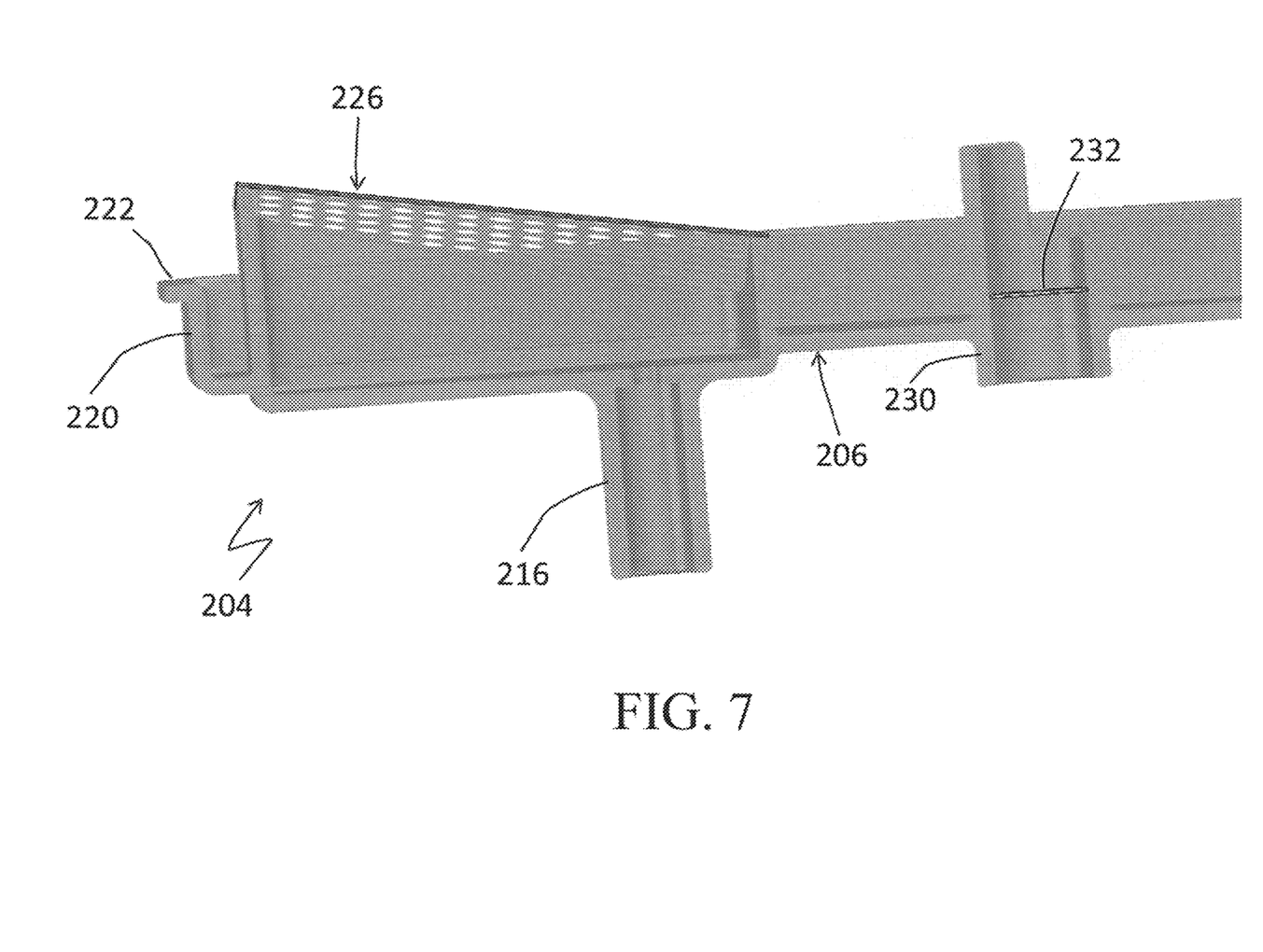
FIG. 7 is a perspective bottom angled cross sectional view of the blood chamber lid shown in FIG. 4.

As shown, the blood chamber lid 104 is desirably a one piece device that can desirably serve as or otherwise provide a closing an open ended blood chamber 102. To that end, the blood chamber lid 104 may form and include a generally planar top wall 106 having an outlined planar shape 110 that generally conforms to an outlined planar shape 112 of the open end 114 of the blood chamber 102, with the lid top wall 106 forming or including an inlet 116 to the blood chamber 102. The blood chamber 102 may include an outlet (not shown) such as may appropriately be disposed in the bottom or other selected portion of region of the chamber, such as known in the art.

The blood chamber lid 104 can also desirably include a peripheral side wall 120 such as generally perpendicularly extending from the top wall 106. The peripheral side wall 120 may include a collar portion 122 or other peripheral features such as to matingly seal the lid 104 with the chamber 102, such as via a lateral side wall 124 of the blood chamber 102.

The one piece blood chamber lid 104 also includes, incorporates or otherwise appropriately integrates therein a selected blood filter or treatment media 126 spaced apart from the inlet 116. The blood filter or treatment media 126 can serve to filter, treat or otherwise process the blood passing through the inlet 116 upon entry into the blood chamber 102 with the filter media 126 filtering or otherwise separating gross particulate, clots, clumps of platelets, and the like, for example, from the blood passing therethrough.

While the broader practice of the invention is not necessarily limited by or to specific methods or techniques by which a desired blood filter or treatment media is incorporated into a blood chamber lid, particularly useful methods or techniques for incorporating a desired blood filter or treatment media into a blood chamber lid include heat sealing or ultrasonic welding a blood filter or treatment media with a material forming the lid.

The one piece blood chamber lid 104 further also includes, incorporates or otherwise appropriately integrates therein a vent port 130. The vent port 130 allows air to vent from the blood chamber 102. The vent port 130 is desirably covered or spanned such as by a vent cover 132 such as in the form of a mesh material such as of an acrylic copolymer or other selected material to prevent or avoid unintended entry of material into the blood chamber via the vent port. Those skilled in the art and guided by the teachings herein provided will understand and appreciate that such venting can desirably serve to equalize pressure between the chamber and the atmosphere without introducing outside atmospheric contaminants into the system.

Thus, a blood chamber lid in accordance with a preferred practice of the subject development serves to not only close or seal a blood chamber but also serves as or otherwise forms an attachment point for a blood filter and chamber vent. The blood chamber lid integrates the blood filter and vent into the lid. Such a blood chamber lid device desirably utilizes a generally flat or planar filter and an over molded vent such as to simplify molding and assembly. A simplified blood chamber lid design such as herein provided allows a single component to function and perform multiple functions, including: providing or securing closure to the blood chamber; providing treatment such as in the nature of filtration or separation of the blood passing into the chamber via the inlet; as well as providing for the venting, discharge or release of air or gaseous material, for example. Those skilled in the art and guided by the teachings herein provided will understand and appreciate that a blood chamber lid such as herein provided and such as may serve and/or fulfill multiple functions such as one or more and preferably each of the three functions identified above allows for ease of assembly for both the customer and supplier such as by reducing the number of bonds/components, for example.

FIGS. 4-7 illustrate a blood chamber lid 204 in accordance with another embodiment of the subject development. The blood chamber lid 204, similar to the blood chamber lid 104 shown in FIGS. 1-3 and described above, is desirably a one piece device that can desirably serve as or otherwise provide a closing an associated open ended blood chamber (not shown). To that end, the blood chamber lid 204 may form and include a generally planar top wall 206 having an outlined planar shape that conforms to an outlined planar shape of the associated blood chamber open end, with the top wall 206 forming or including an inlet 216 for the associated blood chamber.

The blood chamber lid 204 also desirably includes a peripheral side wall 220 such as generally perpendicularly extending, from the top wall 206. The peripheral side wall 220 may include a collar portion 222 or other peripheral features such as to join or seal the lid 204 with the chamber.

The one piece blood chamber lid 204 also includes, incorporates or otherwise appropriately integrates therein a selected blood filter or treatment media 226 spaced apart from, the inlet 216. The blood filter or treatment media 226, similar to the blood filter or treatment media 116 of the blood chamber lid 104 described above, can serve to filter, treat or otherwise process the blood passing through the inlet upon entry into the blood chamber with the filter media filtering gross particulate and the like from the blood passing therethrough.

The blood filter or treatment media 226, however, primarily differs from the blood filter or treatment media 126 in that the blood filter or treatment media 226 is a multiplanar element having a slope angled away from the inlet 216 and toward a lateral side wall of the chamber. More specifically, the blood filter or treatment media 226 is composed of a first planar element 227 and a second planar element 228 each sloped toward opposed extended longitudinal sides such that the filter media 226 can work as a flow director, directing the blood towards the side walls of the associated chamber.

While the blood filter or treatment media 226 is shown as generally composes of first and second planar elements, those skilled in the art and guided by the teachings herein provided will understand and appreciate that the broader practice of the invention is not necessarily so limited. For example, the invention can be practiced employing a blood filter or treatment media composed of 3, 4, or more such planar elements such as may be desired for particular applications.

The one piece blood chamber lid 204, similar to the blood chamber lid 104 described above, may suitably include, incorporate or otherwise appropriately integrate therein a vent port 230. The vent port 230 allows air or other gaseous material to vent from the blood chamber. The vent port 230 is desirably covered or spanned such as by a vent port cover 232 such as in the form of a mesh material such as of an acrylic copolymer or other selected material to prevent or avoid unintended entry of material into the blood chamber via the vent port.

As will be appreciated by those skilled in the art and guided by the teachings herein provided blood chamber lids in accordance with one preferred aspect of the invention desirably include or otherwise effectively incorporate multiple, otherwise normally separate features, such as to achieve filtration of the blood and venting of air prior to reentry of the blood to the patient's bloodstream.

Moreover, whereas in customary manufacture and assembly processing blood filters and vent caps are separately produced in separate machines and then subsequently assembled with a lid by a customer such as by solvent bonding, the complexity of the assembly process for the manufacturer and/or the user is dramatically simplified by the development and use of a blood chamber lid such as herein provided. For example, as described above, a blood chamber filter and a blood chamber vent can desirably be directly integrated in or with a blood chamber such as via molding/automated assembly. This reduces or minimizes process steps, quality issues, and/or costs.

Also, whereas current methods of blood filter manufacture typically produce particulates and thus necessitate additional processing steps and/or precautions, integration of a blood chamber filter and/or blood chamber vent port mesh material, such as in accordance with a preferred practice of the subject development can significantly reduce or avoid such particulate production and thus represents a further improvement over the prior art.

It is to be understood that the broader practice of the invention is not necessarily limited by or to practice with particular materials of construction as for example a variety of materials, such as including various plastic materials, for example, can be used for the lid, vent cover/filter, and/or blood filter, respectively. In accordance with certain preferred embodiments the lid can desirably be made or constructed of acrylic. The vent cover/filter can desirably be an acrylic copolymer. The blood filter can desirably be a PET screen.

In one embodiment, a filter media is desirably heat sealed or ultrasonic welded with a lid, such as a lid formed of acrylic material.

It is to be further understood and appreciated that the numerous above-identified and/or described features of the subject blood chamber lid can be appropriately practiced alone or individually or in various combinations as may be desired for particular or specific applications.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A lid for closing an open ended blood chamber, the lid comprising:
    a one piece device forming an inlet to the blood chamber, the one piece device including a filter media spaced apart from the inlet and wherein blood passing through the inlet passes through the filter media upon entry into the blood chamber with the filter media filtering gross particulate from the blood passing therethrough, the one piece device further including a vent port with an associated vent port cover to allow air to vent from the blood chamber; and
    wherein the filter media is a multi-planar element having a slope angled away from the inlet and toward a lateral side wall of the chamber, wherein faces of the multi-planar element are conjoined at obtuse angles, and comprise a major conjoint line sloping away from the inlet and towards the lateral side wall.

2. The lid of claim 1 wherein the one piece device has an outline planar shape that conforms to an outline planar shape of the blood chamber open end.

3. The lid of claim 2 wherein the one piece device comprises a planar top wall and a peripheral side wall to matingly seal with a lateral side wall of the blood chamber.

4. The lid of claim 1 wherein at least one of the filter media and the vent port cover are directly molded with a plastic material forming the lid.

5. The lid of claim 1 wherein the lid comprises an acrylic material.

6. The lid of claim 1 wherein the filter media comprises a PET Screen.

7. The lid of claim 1 wherein the vent port cover comprises a mesh material.

8. The lid of claim 7 wherein the vent port cover comprises an acrylic copolymer.

9. The lid of claim 1 wherein the filter media is one of heat sealed or ultrasonic welded with a material forming the lid.

10. A lid for closing an open ended blood chamber, the lid comprising:
    a one piece device forming an inlet to the blood chamber, the one piece device having an outline planar shape that conforms to an outline planar shape of the blood chamber open end, the one piece device including a filter media spaced apart from the inlet and wherein blood passing through the inlet passes through the filter media upon entry into the blood chamber with the filter media filtering gross particulate from the blood passing therethrough, the filter media comprising a multi-planar element integrated into the one piece device, the one piece device further including a vent port with an associated vent port cover to allow air to vent from the blood chamber, wherein the vent port is over molded into the one piece device; and
    wherein the a multi-planar element comprises a slope angled away from the inlet and toward a lateral side wall of the chamber, wherein faces of the multi-planar element are conjoined at obtuse angles, and comprise a major conjoint line sloping away from the inlet and towards the lateral side wall.

11. The lid of claim 10 wherein the one piece device comprises a planar top wall and a peripheral side wall to join and seal with a lateral side wall of the blood chamber.

12. The lid of claim 10 wherein at least one of the filter media and the vent port cover are directly molded with a plastic material forming the lid.

13. The lid of claim 10 wherein the lid comprises an acrylic material.

14. The lid of claim 10 wherein the filter media comprises a PET Screen.

15. The lid of claim 10 wherein the vent port comprises a mesh material.

16. The lid of claim 15 wherein the vent port cover comprises an acrylic copolymer.

17. The lid of claim 10 wherein the filter media is one of heat sealed or ultrasonic welded with a material forming the lid.

18. A lid for closing an open ended blood chamber, the lid comprising:

a one piece device forming an inlet to the blood chamber, the one piece device at least in part formed of an acrylic material and including a filter media at least one of heat sealed or ultrasonic welded with the acrylic material forming the lid, the filter media spaced apart from the inlet and wherein blood passing through the inlet passes through the filter media upon entry into the blood chamber with the filter media filtering gross particulate from the blood passing therethrough, the one piece device further including a vent port with an associated vent port cover to allow air separated to vent from the blood chamber, the vent port cover comprising an in molded mesh material; and wherein the filter media is a multi-planar element having a slope angled away from the inlet and toward a lateral side wall of the chamber, wherein faces of the multi-planar element are conjoined at obtuse angles, and comprise a major conjoint line sloping away from the inlet and towards the lateral side wall.

19. The lid of claim 18 wherein the one piece device has an outline planar shape that conforms to an outline planar shape of the blood chamber open end, the one piece device comprising a planar top wall and a peripheral side wall to matingly seal with a lateral side wall of the blood chamber.

* * * * *